United States Patent [19]
Maire et al.

[11] Patent Number: 5,345,478
[45] Date of Patent: Sep. 6, 1994

[54] METHOD AND DEVICE FOR NON-DESTRUCTIVE EXAMINATION OF A WALL OF A TANK CONTAINING A RADIOACTIVE LIQUID

[75] Inventors: Daniel Maire, Saint Didier Au Mont D'or; Georges Moreau, Viriat; Jacques Archer, Chatenay-Malabry, all of France

[73] Assignee: Framatome, Courbevoie, France

[21] Appl. No.: 5,067

[22] Filed: Jan. 15, 1993

[30] Foreign Application Priority Data

Jan. 16, 1992 [FR] France .............. 92 00402

[51] Int. Cl.⁵ .......................................... G21C 17/00
[52] U.S. Cl. ................................. 376/249; 376/245
[58] Field of Search ............................ 376/245, 249; 250/358.1, 363.1

[56] References Cited

U.S. PATENT DOCUMENTS

| | | | |
|---|---|---|---|
| 3,994,173 | 11/1976 | Ward et al. | 73/432 R |
| 4,051,369 | 9/1977 | Takeshita | 250/321 |
| 4,463,263 | 7/1984 | Padawer | 250/363 |
| 4,622,200 | 11/1986 | Gold et al. | 376/159 |
| 4,680,470 | 7/1987 | Heald | 250/358.1 |
| 4,704,245 | 11/1987 | Asakura et al. | 376/245 |
| 4,764,338 | 8/1988 | Uchida et al. | 376/313 |
| 4,870,669 | 9/1989 | Anghaie et al. | 378/87 |
| 4,947,045 | 8/1990 | Birks et al. | 250/360 |

*Primary Examiner*—Donald P. Walsh
*Assistant Examiner*—Meena Chelliah
*Attorney, Agent, or Firm*—Pollock, Vande Sande & Priddy

[57] ABSTRACT

The tank contains a liquid in which a radioactive element emitting gamma radiation is distributed substantially uniformly. A photon detector (15) is disposed in the vicinity of the external surface of a measurement, zone of the wall (12), a count is made of the photons emitted by the radioactive element distributed in the liquid (7), through the measurement zone of the wall (12), a number of photons determined by counting is compared with a reference number emitted by the radioactive element through a reference zone of the wall (12) and it is deduced therefrom whether or not a defect (8) is present in the measurement zone of the wall (12). The measurement device comprises a photon detector (15) disposed at one end of a collimator (16) made of heavy metal traversed by channels or windows (17).

6 Claims, 2 Drawing Sheets

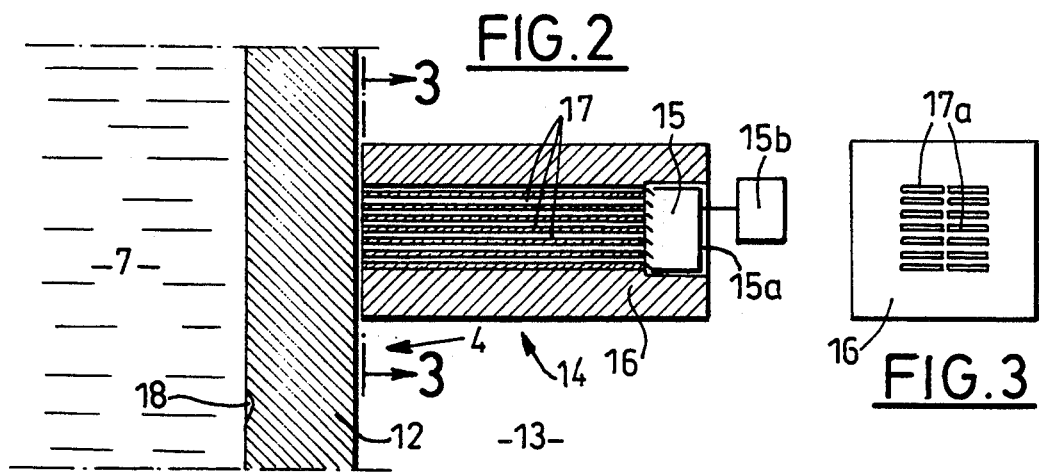
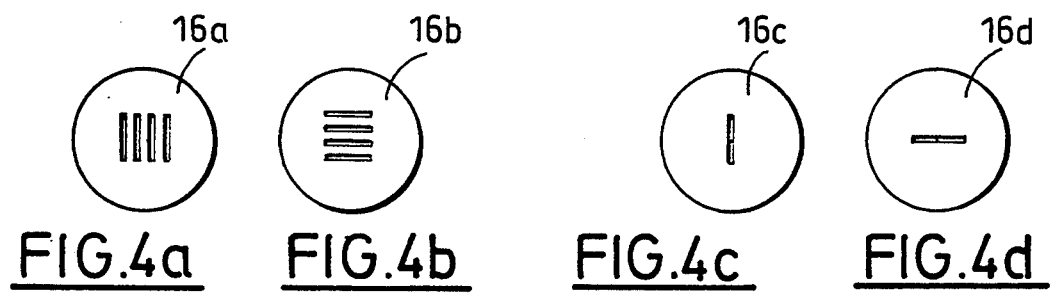
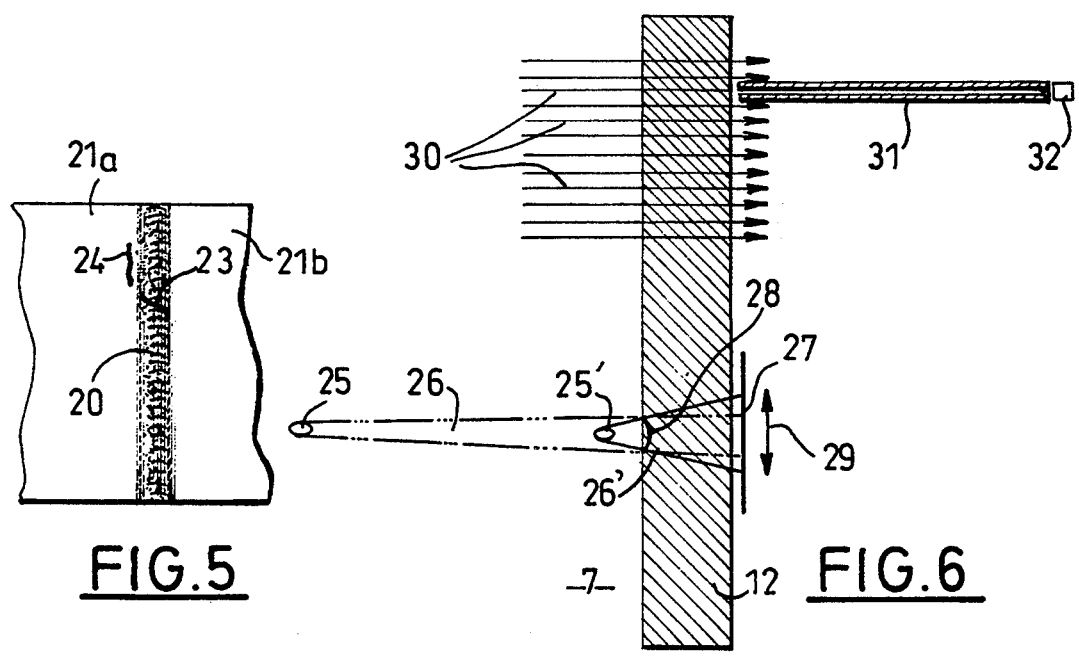

METHOD AND DEVICE FOR NON-DESTRUCTIVE EXAMINATION OF A WALL OF A TANK CONTAINING A RADIOACTIVE LIQUID

FIELD OF THE INVENTION

The invention relates to a method and device for non-destructive examination of a wall of a tank containing a radioactive liquid, and in particular, of a vessel of a fast-neutron nuclear reactor cooled with liquid sodium.

BACKGROUND OF THE INVENTION

Fast-neutron nuclear reactors of the integrated type comprise a vessel of very large dimensions, called a main vessel, which contains the primary cooling fluid of the reactor, generally consisting of liquid sodium in which are immersed the core and the internal structures of the reactor as well as the lower part of the components of the reactor consisting of heat exchangers and pumps which penetrate into the vessel through a slab closing the upper part of the vessel.

The main vessel of the reactor comprises a wall consisting of stainless steel plates shaped and assembled by butt welding along lengthy weld lines.

The main vessel is disposed inside a second vessel, called the safety vessel, so as to form with the safety vessel an inter-vessel space of substantially constant width.

Because of the presence of liquid sodium which is capable of spontaneously igniting in contact with an oxidizing atmosphere, the sodium mass is surrounded by a neutral gas atmosphere, generally consisting of argon which fills, in particular, the inter-vessel space.

Although the manufacture of the vessel of the nuclear reactor is subject to very specific precautions and is accompanied by numerous examinations at all stages of the work, the vessel may include certain defects which do not compromise safety because the probability of their further development is substantially zero. Furthermore, these defects, such as a local deficiency in thickness of a plate forming part of the wall of the vessel, or a deficiency in compactness of a weld, are known because, they have been detected and accepted during manufacture.

In order to detect a highly improbable development of these defects after a certain duration of operation of the reactor, a non-destructive examination is made of the corresponding zones of the walls, at regular intervals, during shutdowns of the nuclear reactor.

Furthermore, since certain defects such as cracks can appear in the wall of the vessel during operation of the reactor, it is necessary to detect such defects as quickly as possible after their appearance.

Various known non-destructive examination techniques, such as radiography, magnetic-particle examination techniques, liquid penetrant examination and ultrasonic or eddycurrent examination methods can be used in order to examine the qualitative state and the integrity of an element of an industrial assembly such as a nuclear reactor.

However, such methods may prove difficult if not impossible for use in examining the wall of the main vessel of a fast-neutron nuclear reactor. The interior of the vessel may not actually be accessed even during periods of shutdown of the reactor, since this vessel contains the core of the reactor which has very high activity and which is filled with hot and radioactive liquid metal.

After the reactor has been put into service, the wall of the main vessel may only be inspected from outside the vessel, the operation having to be remote controlled because of the presence of a neutral gas atmosphere around the vessel, because of the high temperature the vessel which contains hot liquid sodium, even during periods of shutdown of the reactor, and because of intense gamma radiation.

It has been proposed, for conducting the inservice inspection of the wall of the main vessel of a fast-neutron nuclear reactor, to move the inspection means in the inter-vessel space, in the vicinity of the external surface of the main vessel, using a hinged trolley whose movements are remote controlled. However, inspection means which can be associated with the trolley in order simply to conduct the examination of zone or the whole of the main vessel of the nuclear reactor are not known.

Non-destructive examination methods using rays, i.e., photon fluxes of certain energy emitted by a radioactive substance, in the form of a point source, are known.

The photons are capable of passing through a certain thickness of a material to be examined and photon flux passing through the material is modified by the presence of defects. By making a count or a measurement of photon fluxes after passage through the material, it is possible to detect the possible presence of defects in the material.

If a wall is being examined, it is necessary to dispose a gamma-ray emitter and a photon detector on either side of such wall, in corresponding positions. Such a method is therefore not applicable in the case of a main vessel of a fast-neutron nuclear reactor, since it is not possible to place an examination means inside the vessel.

Equally, in the case of a vessel of a pressurized-water nuclear reactor, it is not possible to access the internal volume of the vessel during operation of the reactor, with the result that it is not possible to conduct an inspection of the wall of the vessel in service, using gamma rays emitted by a point source, according to prior art.

In the case of nuclear reactors comprising a vessel containing a liquid for cooling the reactor in which the core is immersed, the cooling liquid may be activated during operation of the reactor, for example under the effect of neutron bombardment.

In the case in which the cooling liquid is sodium, the neutron bombardment coming from the core leads to the formation of two radioactive isotones of sodium, namely sodium-22 and sodium-24. These two elements, which are distributed in the whole of the mass of the liquid sodium filling the vessel, are gamma-ray emitters.

In the case of a nuclear reactor cooled by pressurized water, nuclear reactions occur during the operation of the reactor which lead to the formation of radioactive nitrogen-16 distributed throughout the mass of the primary water filling the vessel. The nitrogen-16 continuously formed in the vessel of the reactor in operation emits gamma rays because of its radioactivity.

Receptacles or tanks which are intended to contain liquids containing one or more gamma-ray emitter radioactive elements distributed in the mass of the liquid contained in the tank are more generally used in the nuclear industry.

A radioactive element contained and distributed in the mass of a liquid contained by a tank has to date never been used in order to perform the non-destructive examination of the wall of the tank.

SUMMARY OF THE INVENTION

It is an object of the invention is therefore to provide a method for non-destructive examination of a wall of a tank containing a liquid in which at least one radioactive element emitting gamma radiation is distributed substantially uniformly, consisting of counting photons in the vicinity of the external surface of a measurement zone of the wall and comparing the number of photons determined by counting with a reference number of photons, in order to deduce therefrom whether or not a defect is present in the measurement zone of the wall. This enables possible defects in the wall to be detected simply and extremely reliably, without introducing an examination device inside the vessel.

To this end, the count is made of the photons emitted by the radioactive element uniformly distributed in the liquid through the measurement zone of the wall and the reference number is the number of photons emitted by the radioactive element through a reference zone of the wall.

BRIEF DESCRIPTION OF THE DRAWINGS

The invention will now be described, by way of example, with reference to the attached drawings.

FIG. 2 is a sectional view of a device making it possible to implement a method according to the invention for examination of the wall of the main vessel of the nuclear reactor.

FIG. 3 is a front view along line 3—3 in FIG. 2 of a gamma-ray collimation device used for implementing the method according to the invention.

FIGS. 4a, 4b, 4c and 4d are views similar to FIG. 3 showing four variants of a collimation device for gamma rays.

FIG. 5 is a developed view of a weld zone of the wall of the vessel of the nuclear reactor.

FIG. 6 is a schematic sectional view of an examination device according to the invention and by way of comparison of a device for gamma-ray examination according to the prior art.

DESCRIPTION OF THE PREFERRED EMBODIMENT

Figure 1:
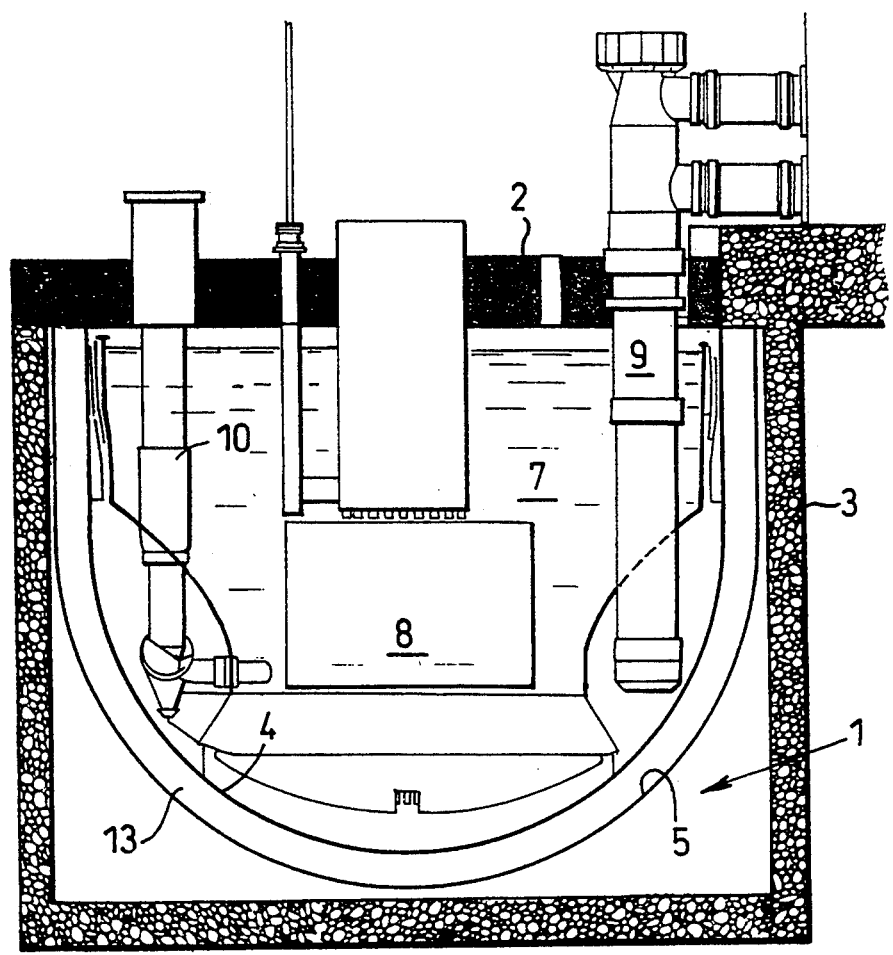
FIG. 1 is a sectional view through a vertical plane of a fast-neutron nuclear reactor cooled with liquid sodium.

FIG. 1 shows a fast-neutron nuclear reactor of the integrated type cooled with liquid sodium. The nuclear reactor comprises a vessel 1 of large dimensions suspended from a slab 2 closing the upper part of the vessel and resting on the concrete structure 3 of the reactor.

The vessel 1 consists of two stainless steel casings 4 and 5 disposed one inside one another with a certain spacing.

The internal casing 4 constitutes the main vessel of the nuclear reactor and the external casing 5 the safety vessel.

The main vessel 4 contains a mass of liquid sodium 7 in which the core 8 of the reactor, consisting of juxtaposed fuel assemblies, is immersed.

The vessel 4 also contains various internal structures supporting the core and separating the internal volume of the vessel into various zones intended to receive liquid sodium at different temperatures.

The circulation of the liquid sodium contained in the vessel between the various zones occurs in particular inside intermediate heat exchangers 9 and by means of pumps 10.

Liquid sodium cooled inside the intermediate exchangers 9 is injected by the pumps 10 to the base of the core, so as to cool the fuel assemblies of the core 8. The upper part of the hot sodium leaving the core 8, in the hot manifold of the nuclear reactor penetrates into the intermediate heat exchangers 9 in which it heats secondary liquid sodium and is cooled before reemerging in the cold manifold of the reactor.

The secondary sodium heated in the intermediate heat exchangers 9 is used for producing steam in steam generators, outside the vessel 1.

The liquid sodium circulating inside the main vessel 4 of the reactor is subjected to intense radiation inside the core and in particular to neutron bombardment by the fast neutrons produced by the core.

Under the effect of the radiation, radioactive isotopes such as sodium-22 ($^{22}$Na) and sodium-24 ($^{24}$Na) are formed by nuclear reaction inside the sodium used as cooling liquid in the vessel.

After a certain duration of operation of the reactor, the cooling sodium inside the vessel therefore has significant radioactivity, in particular because of the presence of radioactive elements such as $^{22}$Na and $^{24}$Na distributed throughout the mass of the sodium.

$^{22}$Na and $^{24}$Na emit photons with a certain energy corresponding to the gamma-ray band.

The half-life of $^{22}$Na is 2.6 years and that of $^{24}$Na is 15 hours.

After shutdown of the nuclear reactor, a certain decrease in the radioactivity of the sodium and in particular in the activity of the radioactive elements $^{22}$Na and $^{24}$Na is therefore produced.

The specific activity of $^{24}$Na is substantially higher than the specific activity of $^{22}$Na.

Within the scope of the invention, consideration has been given to the use of gamma rays emitted by radioactive elements distributed uniformly in the sodium filling the main vessel 4, in order to conduct the examination of the wall of this vessel.

Within the scope of such a use as gamma-ray source for conducting the examination of a wall, only $^{24}$Na has a sufficient activity for the examination to be conducted under satisfactory conditions.

On the other hand, because of its relatively short half-life, the decrease in the activity of this element during the examination is quite perceptible.

As will be explained further on, the examination method according to the invention is implemented in order to take into account this decrease over time.

FIGS. 2 and 3 represent a device making it possible to implement the method according to the invention for conducting the examination of the wall 12 of the main vessel 4 of the nuclear reactor containing, after a certain duration of operation of the reactor, a mass 7 of radioactive liquid sodium containing in particular sodium-24.

The examination is conducted after shutdown of the nuclear reactor, i.e., after the control rods have been engaged in their position of maximum insertion inside the core 8 and after a period with a duration which may be of the order of 35 hours after shutdown of the reactor, during which the activity of the reactor substantially decreases.

In this manner, exposure of the device used for the examination to radiations which were too intense for the materials making up this device to withstand during the period of exposure, is avoided.

This also avoids excessive interference of the radiation coming directly from the core with radiation coming from the mass of cooling sodium, which would make the measurements difficult to analyze.

As shown in FIG. 2, the device 14 used for the examination is introduced inside the inter-vessel space 13 made between the wall 12 of the main vessel 4 and the safety vessel 5.

The device 14 comprises a photon detector 15 comprising a sensitive surface 15a connected by a conductor to an electronic processing module 15b and a collimator 16 made of lead or lead-based heavy alloy comprising windows and collimation channels 17 aligned with the sensitive surface 15a of the photon detector 15.

As shown in FIGS. 2 and 3, the collimator 16 may consist of a block of lead or of heavy alloy of overall parallelepipedal shape comprising a housing for the photon detector 15 at one of its ends and longitudinal channels 17 having in cross-section the shape of slits which constitute the windows 17a of the collimator, as seen in FIG. 3.

In the embodiment represented in FIGS. 2 and 3, the windows 17a constituting the entry parts of the channels 17 in the vicinity of the wall 12 are disposed in two mutually parallel rows.

The gamma rays consisting of photons having a certain energy are directed from the mass of radioactive sodium 7 in which is distributed the gamma emitter consisting of sodium-24, as far as the sensitive surface 15a of the detector 15, through the wall 12 and the channels 17 of the collimator 16.

An examination is successively conducted of measurement zones of the wall whose cross-sections correspond to the cross-section of the entry part of the collimator, i.e., to the cross-section of the piece made of lead or heavy alloy traversed by the channels 17.

If the zone of the wall 12 situated opposite the examination device 14 is completely sound and has no defect, the number of photons emitted by the sodium 7, through the measurement zone of the wall, during a given time interval, depends only on the activity of the radioactive element, i.e., of the sodium-24 contained in the mass of sodium 7.

On the other hand, in the case of the presence a defect such as 18 such as a crack, in the wall 12, the number of photons emitted through the wall 12 by the radioactive element contained in the sodium 7 is different from that which it would be in the case of passage through a zone of the wall which is sound.

By comparing the number of photons emitted through a reference zone and through the measurement zone, it is possible to determine whether the wall has at least one defect in the measurement zone.

In general, the number of photons emitted through a zone which has defects such as cracks is greater than the number of photons emitted through a zone of the wall which is sound.

Various types of processing may be implemented using an adapted electronic module.

In a first type of processing, it is possible to count the photons reaching the detector 15 until a certain number of photons is reached and to measure the time necessary for the emission and counting of this predetermined number of photons.

In the case in which the count is made in front of a zone of the wall 12 which is sound and comprises no defect, the counting time until a predetermined number photons is reached depends only on the activity of the sodium-24 in the mass of liquid sodium 7, i.e., on the time which has elapsed since the end of the decay period after the shutdown of the reactor.

A calibration is previously made in order to define the relationship between the time necessary for counting the predetermined number of photons and the time which has elapsed since the end of the period of decay of the activity.

In the case in which a difference is detected between the time thus defined as a function of the measurement period and the time necessary for the counting, the presence of a defect in the wall is deduced therefrom.

In general, the counting time is then less than the time defined by the relationship.

In the case of a fast-neutron nuclear reactor and a count made by a photon detector in the inter-vessel space after a decay period of 35 hours following the shutdown of the reactor, the activity of the sodium-24 is decreased by half over a period of 15 hours.

It has been possible to make a count of a representative number of photons which is usable for the detection during a period of one second at the start the measurement period, this duration rising to two seconds after a duration of 15 hours.

During the 15 hour period, the normal duration of counting of the predetermined number of photons, i.e., the duration of counting of the predetermined number of photons through a zone of the wall which is sound varies substantially linearly between one and two seconds.

It is thus possible, for a measurement made within 15 hours following the radioactivity-cooling period to determine whether the duration of counting of the defined number of photons corresponds to a zone which is sound or to a zone which has defects.

The method according to the invention could be implemented in a second manner by using two identical measurement devices 14, one of these devices being moved in a measurement zone capable of having defects and the other measurement device being moved in a zone of the wall which is sound.

In the case of the examination of a weld bead 20 between two stainless steel plates 21a and 21b making up a part of the wall 12 of the vessel of the nuclear reactor, one of the measurement devices 14 is moved along the weld bead 20 so as to cover the width of this weld bead and two narrow lateral strips on either side of the weld bead and the other measurement device is simultaneously moved in a zone of one of the plates 21a or 21b which is remote from the weld bead 20.

A difference in the number of photons counted by the two measurement devices 14 is recorded in the case in which a defect 23 is present inside the weld bead 20 or in the case in which a defect such as a crack 24 is present in one of the plates, in the vicinity of the weld bead 20, the defects 23 and 24 being formed at the moment of welding of the plates.

It has been possible, by the method of the invention, to examine of butt welds of steel plates of 25 mm thickness making up parts of the wall of a fast-neutron nuclear reactor vessel, so as to detect defects whose mean characteristics are the following:

width: 0.1 mm
length: 20
depth (inside the weld bead or the plate): 5 mm.

Counting the photons passing through the measurement zone capable of having defects and comparing the number obtained with a reference number also makes it possible to determine the relative volume of the defect in the measurement zone.

It has been possible to conduct this examination satisfactorily, using gamma rays emitted by sodium-24 distributed in the mass of sodium contained by the vessel, the counting time being generally between one and two seconds. It is thus possible to make a sweep of the zones of the vessel to be monitored by placing the detection and counting device in successive measurement zones, for a duration of between one and two seconds.

Before conducting the examination of the set of weld zones of the vessel or of the entire wall, it is possible simultaneously to use an appropriate number of measurement devices in various zones of the vessel.

As a function of the shape and the size of the zones of the vessel to be examined, it is possible to use collimators of different forms and for example collimators consisting of large cylindrical pieces of circular cross-section made of lead or lead alloy, for example DENAL, as show in FIGS. 4a, 4b, 4c and 4d.

The collimator 16a represented in FIG. 4a comprises four windows in the shape of slits disposed in the vertical direction.

The collimator 16b represented in FIG. 4b comprises four windows in the shape of slits disposed horizontally and placed one above the other.

The collimator 16c represented in FIG. 4c comprises a single window consisting of a vertical slit, while the collimator 16d represented in FIG. 4d comprises a single horizontal window consisting of a slit.

The photon detector should be sensitive only to radiation coming directly from the sodium 7 though the wall 12 and not to radiation from another source, e.g., radiation scattered in the thickness of the wall.

It is therefore necessary to perform filtering by means of a gamma spectrometer associated with the operation and measurement assembly and to use a collimator made of lead or heavy alloy at the exit end of which the sensitive surface of the photon detector is placed.

FIG. 6 represents, schematically and comparatively, gamma-radiography detection means according to the invention in the upper part of the figure and according to the prior art in the lower part of the figure.

In the case of the devices according to the prior art, a gamma-ray source 25 or 25' of small size (a few millimeters) was used which could be considered as a point source. The source 25 or 25' emits a photon beam 26 or 26' in the direction of a film or of the sensitive surface of a detector 27.

As the figure shows, it is necessary, in order to detect a defect 28 in the wall 12 as clearly as possible, to place the gamma-ray source as far as possible from the internal surface of the wall 12, so as to decrease the extent of the zone of the sensitive surface receiving the photon emission (zone 29).

The position 25 of the gamma source is therefore preferable to the position 25', inasmuch as the extent of the zone 29 corresponding to the defect 8 is much less spread out in a geometrically blurred shape in the case of the distant source 25.

Because the gamma source 25 or 25' and the sensitive surface 27 must be placed on opposite sides of the wall 12, the method according to the prior art cannot be used for examining the wall of the main vessel of a fast-neutron nuclear reactor.

In the case of gamma radiation emitted by sodium 24 distributed in the mass of sodium 7 contained by the wall 12, the radiation passes substantially uniformly through all the zones of the wall, as schematically represented by the parallel beams 30 of gamma rays.

By using a collimator 31 whose width is substantially equivalent to the distance from the source 25 to the wall 12, the defect definition obtained on the sensitive surface of the detector 32 is equivalent to that obtained by a gamma-ray point source distant from the wall 12, such as the source 25.

This result is obtained by virtue of a collimator/detector assembly disposed on only one side of wall 12.

In the case of a tank containing a radioactive liquid, such as a nuclear reactor vessel, it is therefore possible to detect defects of the wall of the tank with precision, by placing a detector in successive measurement zones outside the wall and by using a collimator.

It is of course necessary for the radioactive liquid contained in the tank to contain a gamma-ray emitter radioactive element which has sufficient activity and is uniformly distributed in the mass of the liquid.

Figure 7:
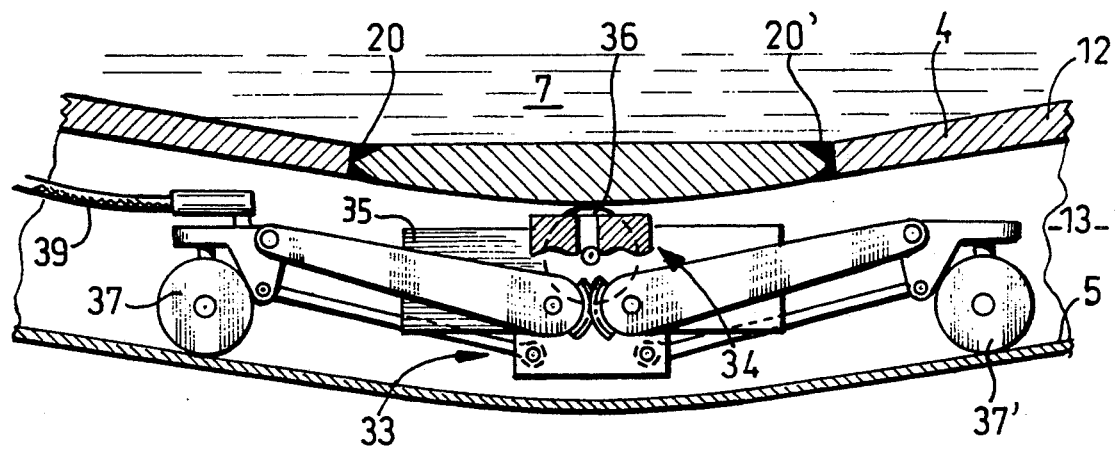
FIG. 7 is a sectional view through a vertical plane of a device making it possible to move a photon detector in the inter-vessel space of a nuclear reactor in order to conduct the examination according to the invention.

In the case of the examination of the main vessel of a fast-neutron nuclear reactor cooled with liquid sodium, it is possible to use, as represented in FIG. 7, a conventional trolley 33, moving in the inter-vessel space 13 between the main vessel 4 of the reactor containing a mass of sodium 7 and the safety vessel 5.

The trolley 33 comprises a support 35 onto which a measurement device 34 is fixed, which measurement device is moved using the trolley 33 in the vicinity of the wall 12 of the safety vessel 4 and in particular in the region of the weld zones 20 and 20'.

The trolley 33 comprises in a known manner arms hinged onto the support 35 at the end of which are mounted roller bearing means 37 and 37' which come into rolling contact with one of the vessels (for example the safety vessel 5).

The trolley 33 also comprises roller bearing means such as 36 which come into contact with the second vessel (here the main vessel 4).

The position of the hinged arms may be controlled by jacks in order to maintain the contact between the roller bearing elements and the walls between which the trolley 33 moves.

The trolley 33 is motorized so as to move itself in the inter-vessel space 13.

The photon detector device 34 made in a similar manner to the device 14 represented in FIG. 2 comprises a detection surface sensitive to photons and a collimator made of lead or heavy alloy comprising collimation windows and guide channels for the photons, at the end which the sensitive detection surface is placed.

The trolley 33 is connected to a cable 39 allowing the motor means of the assembly for moving and holding the trolley 33 to be powered and the measurements coming from the detector assembly 34 to be collected.

In the case of a nuclear reactor cooled with pressurized water comprising a vessel filled witch pressurized water in which the core of the reactor is immersed, it is also possible to conduct an examination of the wall of the vessel by placing a photon detector in successive measurement zones in the vicinity of the external surface of the vessel.

In this case, the measurements will be made during operation of the nuclear reactor.

In fact, radioactive nitrogen-16, which is a gamma-ray emitter element which has sufficient activity for the method of the invention to be implemented, is formed by nuclear reaction in the pressurized water constituting the cooling fluid filling the tank.

The details of implementation of the examination may be substantially identical to those which have been described in the case of the examination of the wall of the vessel of the fast-neutron nuclear reactor.

The method according to the invention therefore makes it possible to conduct the examination of the wall of a tank containing a radioactive liquid simply and without having to introduce a radiation source or detector inside the tank.

Furthermore, the method according to the invention makes it possible to determine with precision, by comparison, whether a defect is present in the wall, in a perfectly defined measurement zone.

The invention is thus not limited to the examination of the vessels of a fast-neutron nuclear reactor cooled with sodium by using the radioactive element $^{24}$Na or the examination of vessels of a pressurized-water nuclear reactor by using nitrogen-16 as the gamma-ray source, but can also be applied to the examination of the wall of any tank containing a liquid containing a radioactive element distributed substantially uniformly throughout the mass of the liquid.

The detection and collimation means or the device for moving these means in the vicinity of the wall may be different from those which have been described.

The invention is useful in the nuclear industry, for examining the wall of any vessel or tank containing a liquid containing a gamma-ray emitter radioactive element.

We claim:

1. Method for non-destructive examination of a wall of a vessel of an operating nuclear reactor containing a cooling fluid of the reactor comprising liquid sodium in which at least a part of the sodium is activated in the operating reactor and constitutes at least one radioactive element emitting gamma radiation distributed substantially uniformly in the cooling liquid of the reactor, said method comprising the steps of:

(a) shutting down the nuclear reactor; and
  (b) counting the number of photons of the gamma radiation emitted by at least one radioactive sodium element through at least a part of the wall of the vessel.

2. Method according to claim 1, wherein said radioactive sodium element is sodium 24.

3. Method according to claim 2, wherein, after shutdown of the reactor and before the counting of photons, the activity of the sodium 24 is decreased during a given period in order to obtain convenient counting conditions.

4. Method according to claim 1, wherein a time interval necessary for counting a predetermined number of photons emitted by the radioactive element through the measurement zone is measured, and the time interval measured is compared with a reference time interval during which the predetermined number of photons is emitted through a reference zone of the wall.

5. Method according to claim 1, wherein a count is simultaneously made of the photons through the measurement zone of the wall (12) and through a reference zone, during a defined time interval, and the number of photons emitted through the measurement zone and through the reference zone is compared.

6. Method according to claim 1, wherein the gamma rays emitted by said at least one element are collimated by passage through a collimator, before reaching a sensitive photon-detection surface.

* * * * *